United States Patent
Karamanoglu et al.

(10) Patent No.: US 8,478,413 B2
(45) Date of Patent: Jul. 2, 2013

(54) BILATERAL PHRENIC NERVE STIMULATION WITH REDUCED DYSSYNCHRONY

(75) Inventors: Mustafa Karamanoglu, Fridley, MN (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/192,256

(22) Filed: Jul. 27, 2011

(65) Prior Publication Data
US 2013/0030498 A1 Jan. 31, 2013

(51) Int. Cl.
*A61N 1/36* (2006.01)
(52) U.S. Cl.
USPC .......................................................... 607/42
(58) Field of Classification Search
USPC .......................................................... 607/42
See application file for complete search history.

(56) References Cited

U.S. PATENT DOCUMENTS

| | | | |
|---|---|---|---|
| 4,901,725 A | 2/1990 | Nappholz |
| 5,056,519 A | 10/1991 | Vince |
| 5,117,824 A | 6/1992 | Keimel |
| 5,265,604 A | 11/1993 | Vince |
| 5,524,632 A | 6/1996 | Stein |
| 5,824,029 A | 10/1998 | Weijand |
| 5,911,218 A | 6/1999 | DiMarco |
| 6,076,015 A | 6/2000 | Hartley |
| 6,463,327 B1 | 10/2002 | Lurie |
| 7,363,085 B1 | 4/2008 | Benser |
| 7,363,086 B1 | 4/2008 | Koh |
| 7,672,729 B2 | 3/2010 | Koh |
| 2005/0085865 A1 | 4/2005 | Tehrani |
| 2006/0276848 A1 | 12/2006 | Min |
| 2008/0161878 A1 | 7/2008 | Tehrani |
| 2008/0288015 A1 | 11/2008 | Tehrani |

*Primary Examiner* — Scott Getzow
(74) *Attorney, Agent, or Firm* — Carol F. Barry (57) ABSTRACT

A system and associated method deliver a respiration therapy. Stimulation pulses are delivered to activate a right portion of a patient's diaphragm and to activate a left portion of a patient's diaphragm. A control processor determines dyssynchrony of a respiratory response to the stimulation pulses and adjusts a stimulation control parameter controlling the delivering of the stimulation pulses in response to dyssynchrony of the respiratory response.

24 Claims, 9 Drawing Sheets

BILATERAL PHRENIC NERVE STIMULATION WITH REDUCED DYSSYNCHRONY

TECHNICAL FIELD

The disclosure relates generally to implantable medical devices and, more particularly, to a method and apparatus for bilateral phrenic nerve stimulation.

BACKGROUND

Stimulation of the right and left phrenic nerves to cause contraction of the diaphragm has been proposed for treating respiratory insufficiency, e.g. in paralysis, apnea, or other respiratory conditions. Phrenic nerve stimulation may be achieved using nerve electrodes implanted in proximity to the phrenic nerve in an open surgical approach. A less invasive approach for implanting electrodes positioned in proximity to a phrenic nerve is a transvenous approach. Electrodes are implanted transvenously, for example in an innominate vein or the superior vena cava (SVC), such that the phrenic nerve is stimulated through the wall of the vein. A need remains for phrenic nerve stimulation methods and associated apparatus for effectively delivering bilateral phrenic nerve stimulation for respiration therapies.

DETAILED DESCRIPTION

In the following description, references are made to illustrative embodiments. It is understood that other embodiments may be utilized without departing from the scope of the disclosure.

Figure 1:
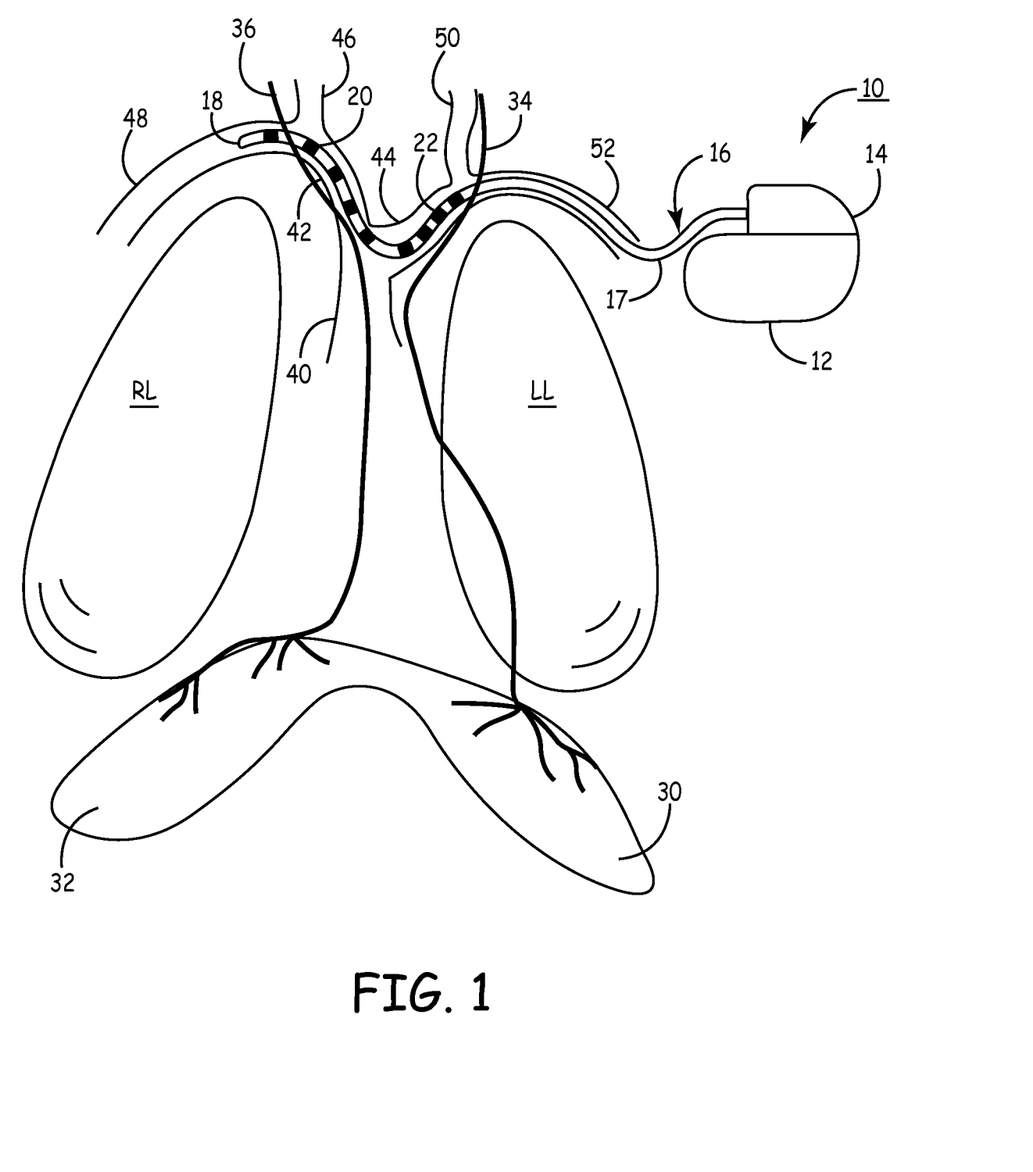
FIG. 1 is a schematic view of an implantable medical device (IMD) system for delivering phrenic nerve stimulation.

FIG. 1 is a schematic view of an implantable medical device (IMD) system for delivering phrenic nerve stimulation. IMD 10 includes a housing 12 enclosing electronic circuitry (not shown) included in IMD 10 and a connector block 14 having a connector bore for receiving at least one medical electrical lead 16 and providing electrical connection between electrodes carried by lead 16 and IMD internal electronic circuitry.

In FIG. 1, the left phrenic nerve 34 and the right phrenic nerve 36 are shown innervating the respective left diaphragm 30 and right diaphragm 32. The anatomical locations of the left phrenic nerve 34, the right phrenic nerve 36 and other anatomical structures shown schematically in the drawings presented herein are intended to be illustrative of the approximate and relative locations of such structures. These structures are not necessarily shown in exact anatomical scale or location. Left phrenic nerve 34 is shown schematically to extend in close proximity to the left internal jugular vein (LJV) 50, the left subclavian vein (LSV) 52, and the left innominate vein (LIV) 44, also referred to as the left brachiocephalic vein.

The anatomical location of the right phrenic nerve 36 is shown schematically to extend in close proximity to the right internal jugular vein (RJV) 46, the right subclavian vein (RSV) 48, the right innominate vein (RIV) 42 (also referred to as the right brachiocephalic vein), and the superior vena cava (SVC) 40.

Lead 16 is a multipolar lead carrying proximal electrodes 22 spaced proximally from distal electrodes 20, positioned at or near the distal end 18 of lead 16. In one embodiment, at least one proximal bipolar pair of electrodes is provided for stimulating the left phrenic nerve 34 and at least one distal bipolar pair of electrodes is provide for stimulating the right phrenic nerve 36. In various embodiments, two or more electrodes may be spaced apart along the lead body, near the distal tip 18 of lead 16, from which at least one pair of electrodes is selected for delivering stimulation to the right phrenic nerve 36. Additionally, two or more electrodes may be positioned along spaced apart locations proximally from the distal electrodes 20 from which at least one pair of electrodes is selected for delivering stimulation to the left phrenic nerve 34.

Lead 16 includes an elongated lead body 17 which may have a diameter in the range of approximately 2 French to 8 French, and typically approximately 4 French to approximately 6 French. The lead body carries the electrodes 20 and 22 which are electrically coupled to electrically insulated conductors extending from respective individual electrodes 20 and 22 to a proximal connector assembly adapted for connection to IMD connector block 14. Lead 16 may be provided with a fixation element for fixing the position of the lead once a desired implant location is identified. Exemplary leads that can be useful for the present disclosure include U.S. Pat. No. 5,922,014, U.S. Pat. No. 5,628,778, U.S. Pat. Nos. 4,497,326, 5,443,492, or U.S. Pat. No. 7,860,580 such that electrodes are added and/or spaced apart in a manner similar to that disclosed in the figures of the present application, all of which are incorporated by reference in their entirety. Additional lead and electrode configurations that may be adapted for use with the present disclosure by adjusting lead shape, length, electrode number and/or electrode to effectively provide phrenic nerve stimulation as described herein are generally disclosed in U.S. Pat. No. 7,031,777, U.S. Pat. No. 6,968,237, and US Publication No. 2009/0270729, all of which are incorporated herein by reference in their entirety.

In one embodiment, distal tip 18 of lead 16 is advanced to a location along the RIV 42 and further along the RSV 48 or the RJV 46 to position distal electrodes 20 in operative relation to right phrenic nerve 36 for delivering stimulation pulses to nerve 36 to activate the right diaphragm 32. The proximal electrodes 22 may be positioned along the LIV 44 or along the junction of the LSV 52 and LJV 50 for delivering stimulation pulses to the left phrenic nerve 34 to activate the left diaphragm 30.

In various embodiments, lead 16 may carry four or more electrodes spaced at selected distances to provide at least one pair near a distal lead tip 18 for right phrenic nerve stimulation and at least one pair more proximally for left phrenic nerve stimulation. In other embodiments, lead 16 may carry multiple electrodes spaced equally along a portion of the body 17 of lead 16 such that any pair may be selected for right phrenic nerve stimulation and any pair may be selected for left phrenic nerve stimulation. Furthermore, it is recognized that in some embodiments, stimulation of only one of the right or left phrenic nerve may be required and an appropriate number and location of electrodes may be provided along lead 16 for such purposes.

Figure 2:
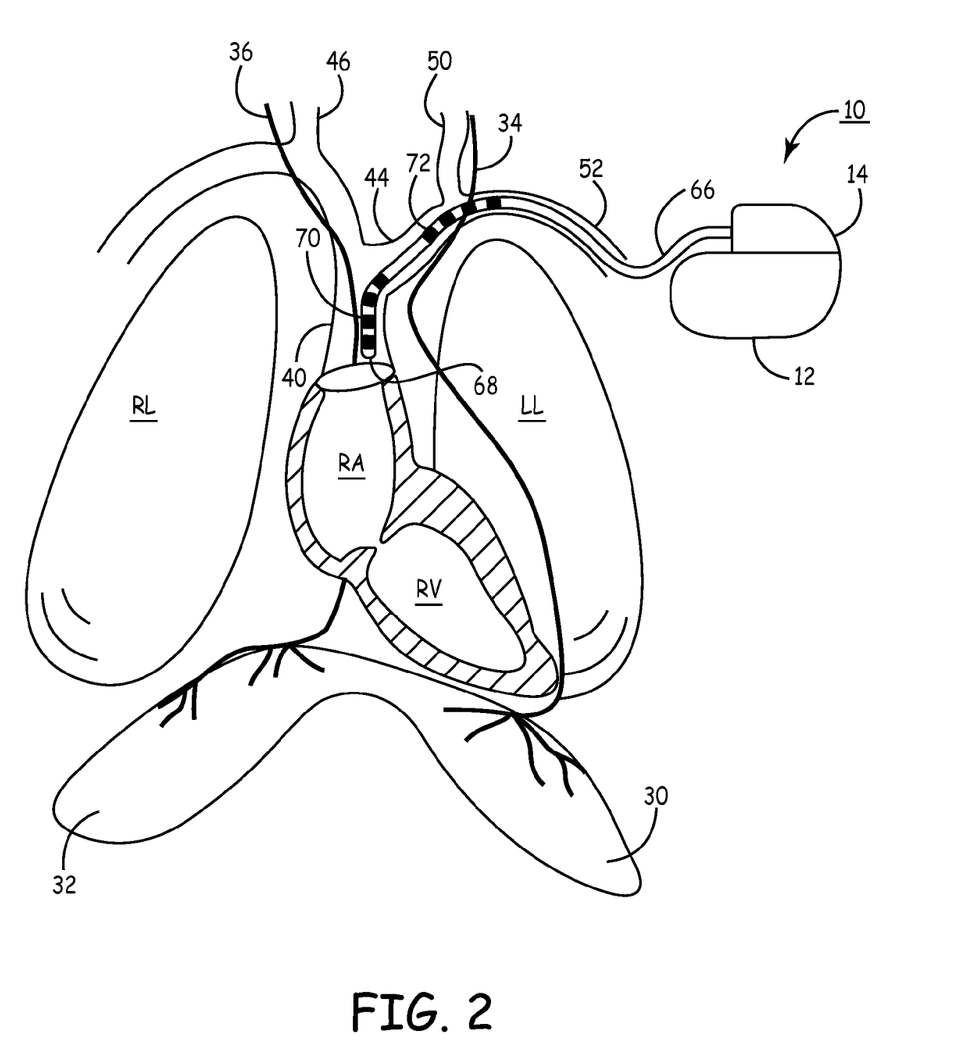
FIG. 2 is a schematic view of an IMD system for delivering phrenic nerve stimulation according to an alternative embodiment.

FIG. 2 is a schematic view of an IMD system for delivering phrenic nerve stimulation according to an alternative embodiment. In FIG. 2, the right atrium (RA) and the right ventricle (RV) are shown schematically in a partially cut-away view. The SVC 40 enters the RA. A lead 66 is coupled to IMD 10 via connector block 14. Lead 66 carries multiple electrodes that may be spaced apart into a plurality of distal electrodes 70 located near distal lead tip 68 and a plurality of proximal electrodes 72. The distal tip 68 of lead 66 is advanced into SVC 40 to position distal electrodes 70 in the SVC 40 for stimulating the right phrenic nerve 36, which extends posteriorly to SVC 40 and the RA. The proximal electrodes 72 are used to stimulate the left phrenic nerve 34, e.g. along the LIV 44 or junction of the LJV 50 and LSV 52.

Figure 3:
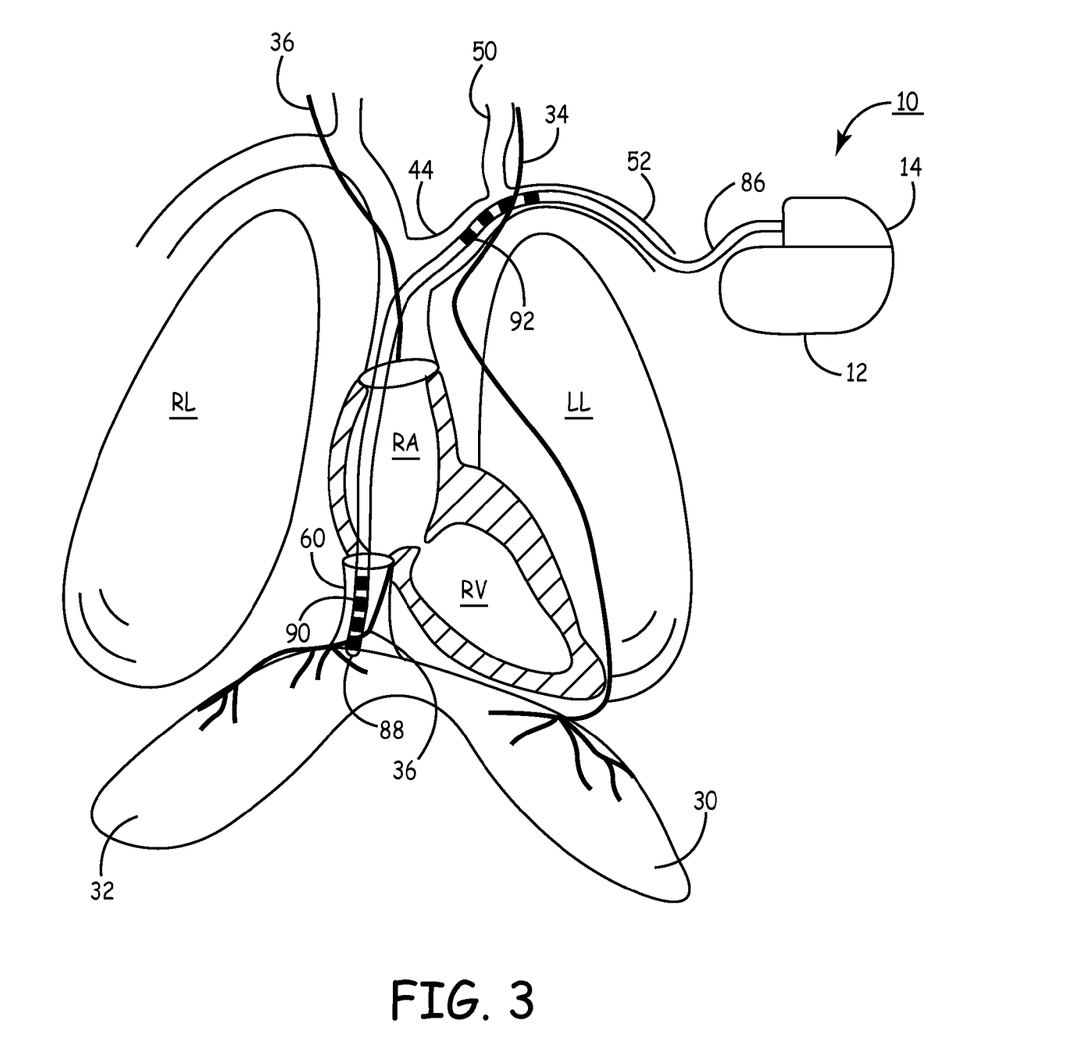
FIG. 3 is a schematic view of an IMD system for delivering phrenic nerve stimulation according to another alternative embodiment.

FIG. 3 is a schematic view of an IMD system for delivering phrenic nerve stimulation according to another alternative embodiment. In FIG. 3, the inferior vena cava (IVC) 60, which empties into the RA, is shown schematically. In this embodiment, lead 86 extends from IMD connector block 14 to the IVC 60 to position electrodes 90, carried by lead 86 at or near distal lead tip 88, along the IVC 60 adjacent the right phrenic nerve 36 near the level of the diaphragm, e.g. approximately at the height of the eighth thoracic vertebra (T8) (not shown). Proximal electrodes 92 are positioned proximally along lead 86 for positioning along the LIV 44 or junction of the LJV 50 and LSV 52 for providing stimulation to the left phrenic nerve 34.

Electrodes used for stimulating the right phrenic nerve and electrodes used for stimulating the left phrenic nerve are shown configured along a common lead in FIGS. 1 through 3. In alternative embodiments it is contemplated that two leads, one for stimulating the left and one for stimulating the right phrenic nerve, may be provided separately.

The housing 12 of IMD 10 may be provided as an indifferent electrode for use in combination with any of the lead-based electrodes shown in FIGS. 1 through 3 for some monitoring purposes. As will be further described below, the electrodes included in an IMD system for delivering a phrenic nerve stimulation therapy may additionally be used for sensing impedance signals. In some embodiments, the housing 12 may provide an indifferent electrode for delivering a drive current during thoracic impedance measurements or used in a measurement pair for monitoring thoracic impedance.

It is further recognized that additional leads and electrodes may be included in an IMD system capable of delivering phrenic nerve stimulation. For example, IMD 10 may be coupled to cardiac leads, which may be subcutaneous leads, transvenous leads positioned in or along a heart chamber, or epicardial leads. IMD 10 may incorporate sensing electrodes along housing 12. IMD 10 may be provided specifically for delivering phrenic nerve stimulation (with associated monitoring of sensed signals for controlling the phrenic nerve stimulation) or may include other therapy delivery capabilities such as cardiac pacing (e.g. for bradycardia pacing, cardiac resynchronizatioin therapy, or anti-tachycardia pacing) cardioversion/defibrillation shocks, drug delivery or the like. As such, the IMD system may include other leads, electrodes and/or catheters not shown in FIGS. 1-3 related to other IMD functions. In some embodiments, electrodes used for delivering phrenic nerve stimulation could be carried by leads that additionally carry cardiac pacing, sensing and/or defibrillation electrodes.

Figure 4:
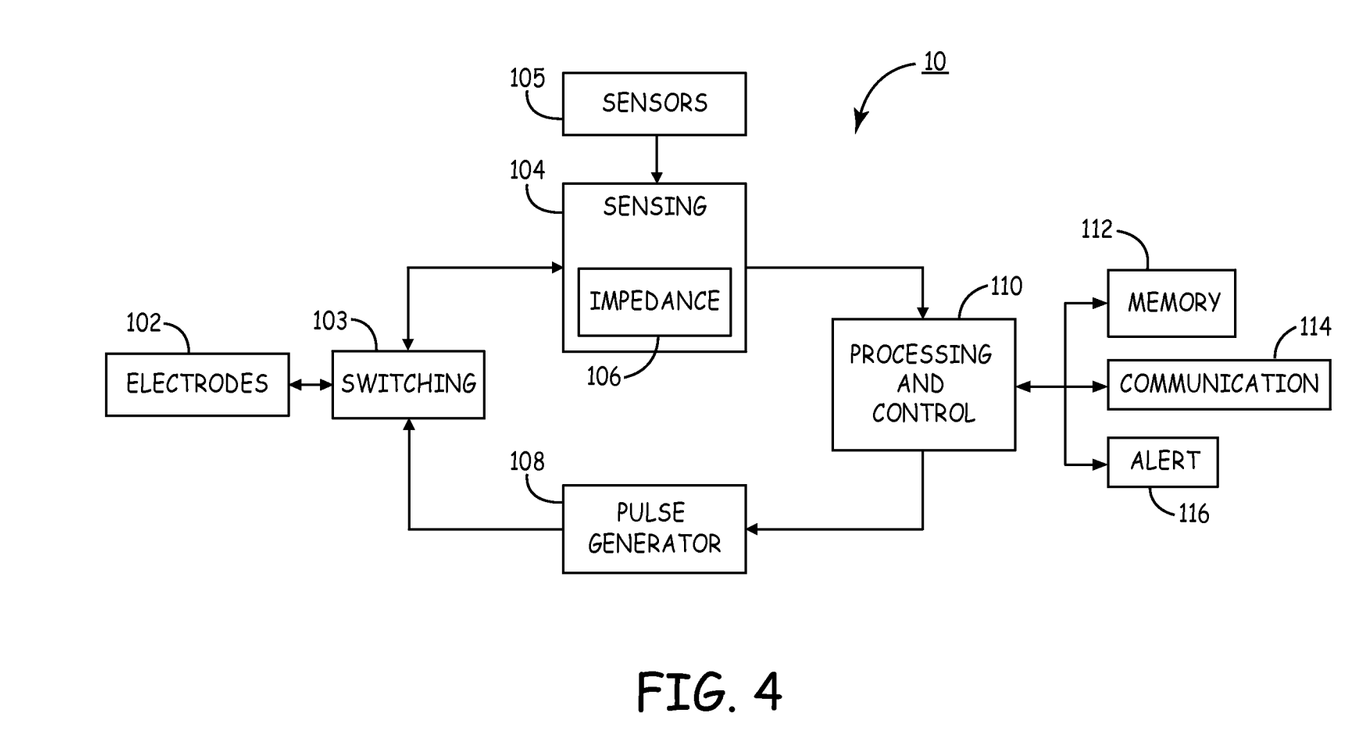
FIG. 4 is a functional block diagram of an IMD that may include any of the leads configured for the implant locations shown in FIGS. 1 through 3.

FIG. 4 is a functional block diagram of an IMD system that may include any of the leads configured for the implant locations shown in FIGS. 1 through 3. Electrodes 102 are coupled to a sensing unit 104, which may include thoracic impedance sensing circuitry 106 in one embodiment, and pulse generator 108 via switching circuitry 103. Electrodes 102 may correspond to any of the electrodes shown in FIGS. 1-3 or other electrodes carried along one or more leads for delivering phrenic nerve stimulation. Electrodes 102 are selected via switching circuitry 103 for monitoring a respiratory response by sensing unit 104, and delivering phrenic nerve stimulation pulses generated by pulse generator 108. Sensing unit 104 and optional sensor(s) 105 are provided for sensing a signal correlated to respiratory activity, which may be measured when phrenic nerve stimulation is being delivered unilaterally, bilaterally or is turned off. In one embodiment, sensing unit 104 measures thoracic impedance signals using impedance sensing circuitry 106 and any available multi-purpose or dedicated electrodes for delivering a drive current and recording an impedance signal.

The impedance sensing circuitry 106 includes drive current circuitry and impedance measurement circuitry for monitoring thoracic impedance. Examples of thoracic impedance measurement methods that can be used for monitoring a respiration signal are generally described in U.S. Pat. No. 4,901,725 (Nappholz), U.S. Pat. No. 6,076,015 (Hartley), and U.S. Pat. No. 5,824,029 (Weijand, et al), all of which are hereby incorporated herein by reference in their entirety. The thoracic impedance measurements can be used to select optimal electrodes and stimulation parameters for achieving a desired effect on respiration caused by phrenic nerve stimulation.

Additionally or alternatively, one or more physiological sensors 105 may be coupled to sensing unit 104 for measuring a respiratory signal. Other sensors may include but are not limited to, EMG electrodes, an accelerometer, a microphone, an air flow sensor, a pressure sensor, or any combination thereof. One or more physiological sensors 105 may be provided to generate a signal correlated to a respiratory response to activation of the right and left portions of the diaphragm. A single signal may be sensed that is responsive to respiratory activity induced by activation of both the right and left portions of the patient diaphragm.

In some embodiments, sensors are provided to produce a "right-side" signal that is more highly sensitive to activation of the right portion of the diaphragm or respiration on the right side of the patient's body and a "left-side" signal that is more highly sensitive to activation of the left portion of the diaphragm or respiration on the left side of the patient body. For example, a first pair of EMG electrodes may be positioned for sensing right diaphragm activation and a second pair of EMG electrodes may be positioned for sensing left diaphragm activation. In another example, a pressure sensor or an accelerometer may be positioned for measuring pressure or motion in the right thoracic cavity and a second pressure sensor or accelerometer may be positioned for measuring pressure or motion in the left thoracic cavity.

Processing and control 110 receives signals from sensing unit 104. In response to received signals, processing and control 110 controls delivery of phrenic nerve stimulation by pulse generator 108. Received signals may additionally include user command signals received by communication circuitry 114 from an external programming device or data acquired from patient images received from an external imaging device such as a fluoroscopy unit.

Processing and control may be embodied as a programmable microprocessor and associated memory 112. Processing and control may be implemented as any combination of an application specific integrated circuit (ASIC), an electronic circuit, a processor (shared, dedicated, or group) and memory that execute one or more software or firmware programs, a combinational logic circuit, or other suitable components that provide the described functionality.

Memory 112 stores data associated with the sensed signals, including impedance signals. Data may be transmitted to an external device by communication circuit 114, which typically includes wireless transmitting and receiving circuitry and an associated antenna for bidirectional communication with an external device. Processing and control may generate reports or alerts that are transmitted by communication circuitry 114.

Alert circuitry 116 may be provided for generating a patient alert signal to notify the patient of a condition warranting medical attention. The patient may be alerted via an audible sound, perceptible vibration, IMD pocket stimulation, or the like and be advised to seek medical attention upon perceiving an alert signal.

Figure 5:
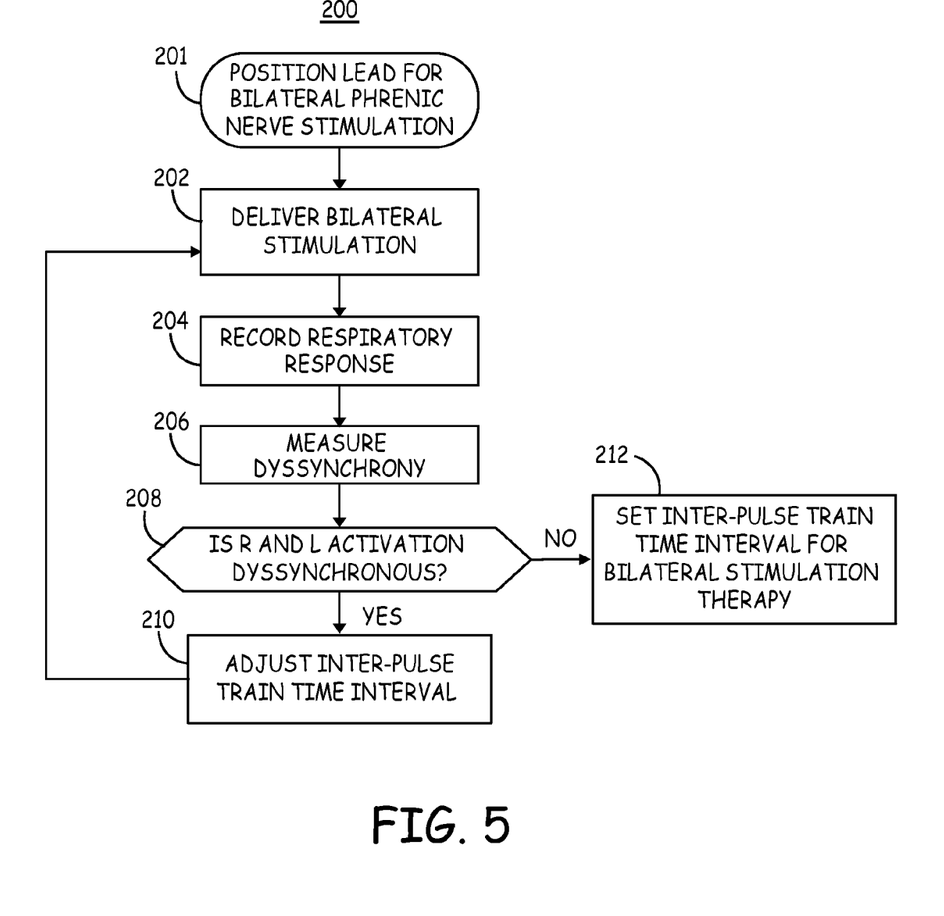
FIG. 5 is a flow chart of a method for controlling phrenic nerve stimulation for delivering a respiration therapy according to one embodiment.

FIG. 5 is a flow chart 200 of a method for controlling phrenic nerve stimulation for delivering a respiration therapy according to one embodiment. During bilateral phrenic nerve stimulation, activation of the right and left hemidiaphragms, also referred to herein as the "right diaphragm" and the "left diaphragm" may become dyssynchronous. The right phrenic nerve is believed to primarily activate the right diaphragm, which tends to be stronger than the left diaphragm in a normal person, and the left phrenic nerve is believed to primarily activate the left diaphragm. When bilateral phrenic nerve stimulation is performed using any of the lead and electrode configurations shown in FIGS. 1-3 or other configurations, the right and left diaphragm portions may be activated at different times. Dyssynchrony of the right and left diaphragm may occur due to stimulation of the right and left nerves at different distances relative to the diaphragm, different conduction velocity of a depolarization signal, different stimulation threshold, different conduction velocity of the right and left diaphragm portions, and other factors.

When dyssynchrony exists between the right and left portions of the diaphragm, the resulting respiration may be less efficient, resulting in lower tidal volume. Accordingly, a bilateral phrenic nerve stimulation method is described herein which addresses dyssynchrony of the right and left portions of the diaphragm during bilateral stimulation and provides for synchronization of the activation of the right and left diaphragm to improve overall respiration for the patient. The illustrative embodiments presented herein describe transvenous bilateral phrenic nerve stimulation. It is recognized, however, that direct phrenic nerve stimulation, for example using a nerve cuff electrode, or direct stimulation to the right and left portions of the diaphragm may be utilized in other embodiments practicing the methods presented herein for synchronizing right and left diaphragm activation.

At block 201, a lead is positioned for bilateral phrenic nerve stimulation. A single lead may be positioned carrying electrodes that may be positioned for transvenous stimulation of both the left and right phrenic nerves according to any of the embodiments shown in FIGS. 1 through 3. Alternatively, two leads may be placed for bilateral phrenic nerve stimulation.

At block 202, bilateral phrenic nerve stimulation is delivered at initial stimulation parameters. Initial stimulation parameters include a pulse amplitude, a pulse number, pulse frequency, stimulation rate (resulting in an induced respiration rate) and a time interval between a pulse train delivered to the right phrenic nerve and a pulse train delivered to the left phrenic nerve. This time interval may be referred to as the R-L time interval or an "inter-pulse train interval" for bilateral phrenic nerve stimulation therapy as it is used to control the timing between a pulse train delivered to the right phrenic nerve and a pulse train delivered to the left phrenic nerve during a given respiration cycle. Adjustment of this time interval is performed to synchronize the activation of the right and left portions of the diaphragm. Initial stimulation parameters may include a default inter-pulse train time interval of 0 ms.

At block 204, a respiratory response is recorded or observed to allow a measurement of dyssynchrony between the right and left portions of the diaphragm at block 206. The respiratory response recorded at block 204 may be a measurement correlated to respiration. A recording of air flow, transthoracic impedance, thoracic motion using an accelerometer or other physiological signal correlated to tidal volume, peak inspiratory air flow, peak expiratory air flow, or other measure of respiration may be recorded at block 204 during bilateral phrenic nerve stimulation. Features of such signals may be used to determine a measure of dyssynchrony at block 206, such as inflection points, double peaks, slope changes or the like caused by dyssynchrony between the right hemidiaphragm and the left hemidiaphragm in a respiration waveform.

Additionally or alternatively, the respiratory response recorded at block 204 may relate to activation of the diaphragm itself. Surface or implanted electrodes may record a right and left EMG signal from the right and left portions of the diaphragm, respectively. Right and left diaphragm EMG recordings allow a time interval to be measured to determine dyssynchrony between the respective right and left activation times of the diaphragm. Diaphragm activation may alternatively be measured using an accelerometer to detect motion of the diaphragm. In still other embodiments, fluoroscopy or other imaging techniques may be used to record an image of diaphragmatic activation to allow a time interval between right and left diaphragm activation times to be observed or estimated at block 206. A clinician may measure dyssynchrony subjectively by palpation of the diaphragm during bilateral phrenic nerve stimulation.

If right and left activation of the diaphragm is found to be dyssynchronous at block 208, based on the dyssynchrony measure determined at block 206, the time interval between pulse trains delivered to the right and left phrenic nerves during a respiration cycle is adjusted at block 210. Adjusting the time interval may include increasing or decreasing the time interval.

After adjusting the time interval, bilateral stimulation is delivered again at block 202 using the adjusted inter-pulse train interval. The respiratory response is again recorded at block 204 to determine if an improvement in R-L synchrony of the diaphragm has been achieved based on the measured dyssynchrony at block 206.

Once the right and left diaphragm activation is satisfactorily synchronized, as determined at decision block 208, the R-L inter-pulse train time interval that resulted in optimized synchronization is stored at block 212 and set as a biphrenic stimulation therapy control parameter.

Figure 6:
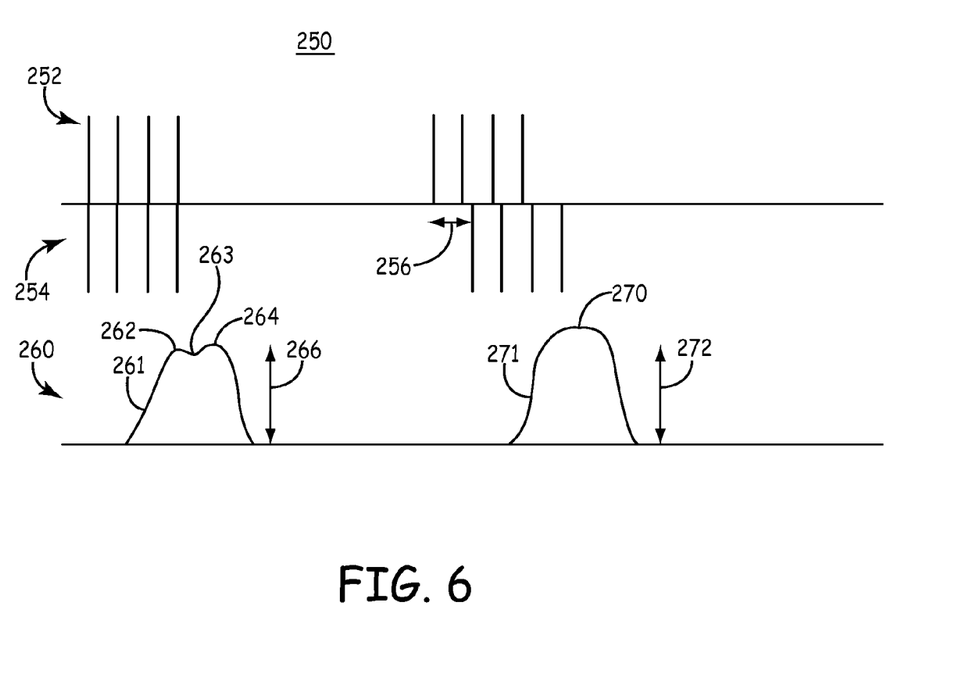
FIG. 6 is a timeline depicting right phrenic nerve pulse trains and left phrenic nerve pulse trains.

FIG. 6 is a timeline 250 depicting right phrenic nerve pulse trains 252 and left phrenic nerve pulse trains 254. A recording of a respiratory response 260 to the pulse trains 252 and 254 is shown. Initially, the respiratory response 260 includes a maximum positive slope 261, double peaks 262 and 264, with an intervening inflection point 263 and a maximum peak measurement 266. The respiratory response 260 is shown schematically and may correspond generally to a thoracic impedance measurement (which increases with increased lung air volume), tidal volume, thoracic or diaphragm motion, or other measures discussed above.

A dyssynchrony measurement may correspond to the time interval between peaks 262 and 264. Alternatively a dyssynchrony measurement may be the detection of double peaks 262 and 264 or detection of the inflection point 263 occurring between peaks 262 and 264. As such, a dyssynchrony measurement may be a quantitative, semi-quantitative or non-quantitative (qualitative) measurement used to detect the presence of dyssynchrony and for detecting an improvement in dyssynchrony in response to adjusting bilateral phrenic nerve stimulation parameters.

The dyssynchrony causing the double peaks 262 and 264 may be caused by the contraction of the right diaphragm lagging the left diaphragm contraction. As such, the inter-pulse train interval is increased from 0 ms to a time interval 256 that causes the right phrenic nerve to be stimulated earlier than the left phrenic nerve. This increased inter-pulse interval improves the synchrony of the right and left diaphragm portions causing a higher maximum positive slope 271, a single peak 270 with an increased peak amplitude 272 compared to amplitude 266. An overall improvement in respiration is achieved by adjusting the inter-pulse train time interval. A dyssynchrony measurement repeated for the second respiration waveform would not find two peaks or an inflection point and thus dyssynchrony would not be detected.

It is contemplated that the time interval between right and left phrenic nerve pulse trains may be adjusted by controlling the start time of the right and left pulse trains by separate time intervals. For example, if delivery of the right and left pulse trains are triggered off of another timing event, such as a detected cardiac R-wave, a timing interval set to control the start of a right pulse train and a second timing interval set to control the start of a left pulse train may be adjusted to have the net effect of an optimized inter-pulse train interval as shown by the illustrative example of FIG. 6. As such, stimulation control parameters used to control delivery of bilateral phrenic nerve stimulation may include an inter-pulse train interval that is adjusted directly. Alternatively, the stimulation control parameters may include other timing parameters that have a net effect of adjusting a resulting inter-pulse train interval.

Figure 7:
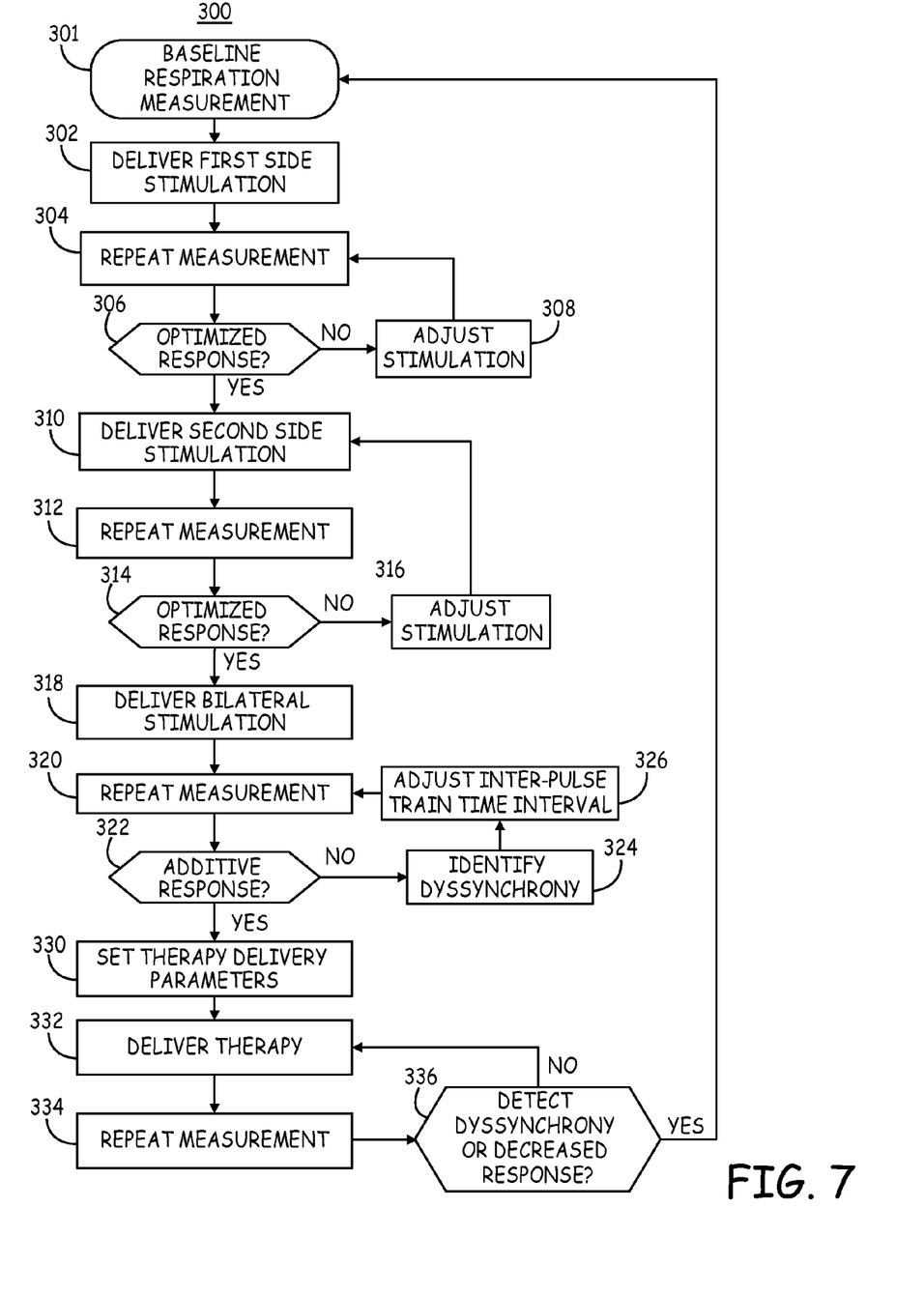
FIG. 7 is a flow chart of a method for controlling bilateral phrenic nerve stimulation according to an alternative embodiment.

FIG. 7 is a flow chart 300 of a method for controlling bilateral phrenic nerve stimulation according to an alternative embodiment. At block 301, a baseline respiration measurement is recorded. The baseline measurement is correlated to respiration, or more generally to respiratory activity, and is obtained before applying any phrenic nerve stimulation. This baseline measurement may be any of the respiratory measurements described above. It is an optional measurement for the purposes of optimizing synchronization between the left and right portions of the diaphragm, but provides a baseline for optimizing the stimulation parameters for obtaining a maximum or acceptable level of improvement in respiratory function overall.

At block 302, one of the right or left phrenic nerves is stimulated using an initial default set of stimulation parameters. The respiration measurement made to obtain a baseline measurement at block 301 is repeated at block 304 during unilateral phrenic nerve stimulation. At block 306, the respiration measurement taken at block 304 is compared to the baseline measurement to determine if an optimized response to the stimulation, or at least some satisfactory improvement in the measurement, is achieved. If the measurement during unilateral stimulation does not show a satisfactory improvement over the baseline measurement, the stimulation parameters controlling the pulse train delivered to the first side are adjusted at block 308.

Adjustment of stimulation parameters may include adjusting pulse amplitude, pulse width, pulse shape, the frequency of pulses within the pulse train, the number of pulses, and the electrodes and electrode polarity selected for delivering stimulation to the first phrenic nerve, right or left. The respiratory measurement is repeated at block 304. This process of adjusting stimulation parameters and comparing a respiratory measurement during unilateral phrenic nerve stimulation to the baseline respiration measurement is repeated until a satisfactory improvement in the respiratory response to the unilateral stimulation is achieved as determined at decision block 306.

At block 310, the second side is unilaterally stimulated beginning with a default set of stimulation parameters controlling pulse trains delivered to the second phrenic nerve. Alternatively, the stimulation parameters found optimal for the first side may be the initial stimulation parameters for the second side. Unilateral phrenic nerve stimulation is delivered to the second side at block 310. The respiration measurement is repeated at block 312 during unilateral stimulation of the second phrenic nerve.

This measurement is compared to the baseline measurement to determine if a satisfactory improvement in respiration has been achieved at block 314. In a similar manner as described above for the first side, the parameters controlling delivery of pulse trains to the second side are adjusted at block 316 until a satisfactory improvement over the baseline respiration measurement is achieved.

At block 318, bilateral stimulation is delivered to the right and left phrenic nerves using the respective right and left pulse train stimulation parameters found to optimize the respiration response to unilateral stimulation of the respective right and left phrenic nerves. Bilateral stimulation (as well as the unilateral stimulation described in the foregoing) may be delivered at a rate higher than the patient's intrinsic respiration rate for one or more respiration cycles. The respiration measurement is repeated at block 320 during the bilateral stimulation. The respiration measurement, during no stimulation, unilateral, or bilateral stimulation, may be performed for one or more cardiac cycles with an average, median, minimum, maximum or other statistical index of the measurement determined.

The respiration measurement during bilateral stimulation is compared to the baseline measurement, each of the unilateral respiration measurements, or any combination thereof. In one embodiment, the respiration measurement during bilateral stimulation is compared to a sum of the respiration measurements made during right and left unilateral stimulation to determine if the bilateral stimulation produces an additive effect of the respiration improvement during right and left unilateral stimulation. The additive effect may be a proportion of the summed respiration measurements taken during right and left unilateral stimulation. Alternatively the differences or ratios between the respiration measurements taken during right unilateral respiration and baseline and during left unilateral respiration and baseline may be compared to the bilateral respiration measurement, individually or in combination.

For example, detection of an additive response at block 322 may be determined based on the following comparison of respiration measurements (RM):

$$RM_{bilateral} - RM_{baseline} \geq P_1 * (RM_{right} - RM_{baseline}) + P_2 * (RM_{left} - RM_{baseline})$$

wherein $P_1$ and $P_2$ may be equal to one or set to different weighting factor values when different contributions of the right and left hemidiaphragms are expected due to injury, disease or the like. It is recognized that the baseline respiration measurement terms ($RM_{baseline}$) terms may be removed and a net constant may be added or subtracted from the right side of the comparison. It is recognized that in various embodiments different criteria may be applied to determine if bilateral stimulation provides a net gain over unilateral stimulation of either the right or left phrenic nerve alone to achieve an optimal or at least satisfactory improvement in respiration during bilateral stimulation as compared to baseline, right unilateral stimulation and left unilateral stimulation.

Furthermore, it is recognized that in various embodiments different combinations of two or more respiration measurements may be determined as a metric or index of the respiration response to no stimulation (intrinsic spontaneous breathing), unilateral stimulation and bilateral stimulation. A metric or index that combines multiple measurements correlated to respiratory activity, which may relate directly to diaphragm activation or measurements of inspiration and expiration or any combination thereof, may be used to detect an additive response of the right and left contributions to respiration.

If an additive response is not detected at block 322, dyssynchrony between the right and left portions of the diaphragm may exist. At block 324, dyssynchrony is identified. Identification of dyssynchrony may be based on the lack of an additive response or based on any of the measurements described in conjunction with FIG. 5. In some embodiments, determining a lack of an additive response to bilateral stimulation at block 322 may trigger additional measurements or analysis of the measurements already taken to determine a measurement of dyssynchrony at block 324.

In response to a lack of or insufficient additive response, and/or any further measurement or assessment of diaphragm dyssynchrony determined at block 324, the inter-pulse train time interval is adjusted at block 326. The respiration response is measured again at block 320 during bilateral stimulation using the adjusted inter-pulse train time interval. This process may be repeated until a maximized or optimized improvement in respiration during bilateral stimulation is achieved. It is contemplated that a maximized respiration response may not always be desirable since a maximal response may lead to diaphragm fatigue. As such, an optimized response or satisfactory improvement in the respiration response may be some percentage improvement over the baseline and/or unilateral stimulation respiration measurements. The amount of such an improvement may vary between embodiments and patients and the particular parameters being measured to gauge the respiration response.

Alternatively, dyssynchrony may be measured at block 324 even when an additive response is detected at block 322 that satisfies some minimum required improvement in the respiratory response during bilateral stimulation. If dyssynchrony is present, a further improvement in respiration may be achieved by adjusting the inter-pulse train time interval at block 326 to improve right and left diaphragm synchronization.

Once the synchrony of the right and left diaphragm portions is optimized through adjustment of the inter-pulse train interval, the stimulation parameters controlling the pulse trains delivered to the right phrenic nerve, the pulse trains delivered to the left phrenic nerve, and the inter-pulse train interval resulting in the optimal respiration response are stored and set as the therapy delivery parameters at block 330.

Bilateral phrenic nerve stimulation therapy is delivered at block 332 according to a programmed protocol. Bilateral stimulation may be delivered for scheduled periods of time, triggered in response to other physiological signals indicating a need for increased respiration, or continuously over a 24 hour period depending on patient need. During stimulation, one or more respiration measurements may be monitored at block 334 to detect a decreased respiratory response and/or evidence of dyssynchrony at block 336, using the methods generally described above. If a change in the respiratory response is detected or dyssynchrony is identified, the process may return to block 326 to adjust the inter-pulse train interval or return to block 301 to repeat the stimulation parameter optimization process.

In one embodiment, an intrathoracic impedance measurement is determined using any of the electrodes available on the phrenic nerve stimulation lead(s), the IMD housing, and/or other electrodes, such as cardiac electrodes, that may be available. A single intrathoracic impedance measurement may be obtained that encompasses portions of the right and left lungs to obtain a single respiration response measurement. Evidence of diaphragm dyssynchrony may be identified based on a decrease in a maximum impedance measurement, double peaks, inflection points, or other features of the impedance waveform.

It is further contemplated that respiration measurements may be obtained that at least partially isolate or separate the responses to bilateral stimulation on the right side (right diaphragm and/or right lung), and the left side (left diaphragm and/or left lung). A measurement or combination of measurements that has higher sensitivity to activation of the right side of the diaphragm and/or filling of the right lung may be obtained along with a measurement or combination of measurements that has a higher sensitivity to activation of the left side of the diaphragm and/or filling of the left lung.

These two right- and left-sided measurements may be recorded simultaneously to identify temporal differences in peak amplitudes, peak slopes or other fiducial point differences in the recorded measurements wherein the temporal difference is correlated to dyssynchrony of the diaphragm.

Figure 8:
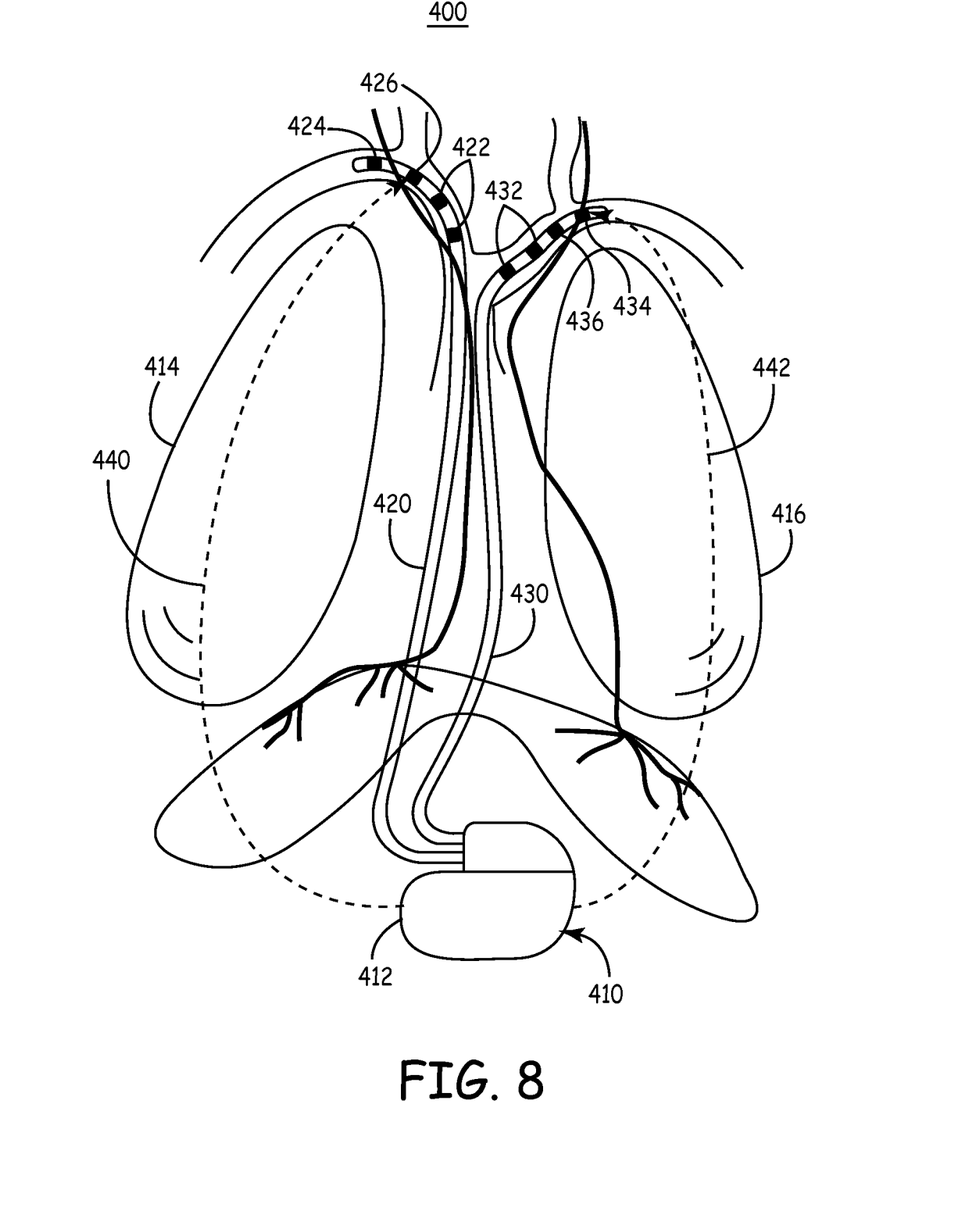
FIG. 8 is a schematic diagram of one IMD system for delivering bilateral phrenic nerve stimulation and measuring right and left thoracic impedance measurements for identifying dyssynchrony of a respiratory response.

FIG. 8 is a schematic diagram of one IMD system 400 for delivering bilateral phrenic nerve stimulation and measuring right and left thoracic impedance measurements for identifying diaphragm dyssynchrony. IMD 410 may be implanted centrally and abdominally and coupled to a right phrenic nerve stimulation lead 420 and a left phrenic nerve stimulation lead 430. The two leads 420 and 430 may alternatively be embodied as a single bifurcated lead. The leads may be extravascular leads implanted in direct contact with the respective right and left phrenic nerves (not shown in FIG. 8). Alternatively, the leads 420 and 430 may alternatively be transvenous leads advanced from a venous access point that allows connection to an abdominal IMD implant location. The lead is advanced through the IVC, right atrium, SVC and to desired venous locations on the right side and the left side, respectively, such as along the right and left innominate veins or subclavian-jugular vein junction. In some embodiments, an indifferent electrode may be carried by a lead and positioned to obtain desired impedance measurement vectors.

One pair of electrodes 422 of lead 420 is used for right phrenic nerve stimulation, and one pair of electrodes 432 of lead 430 is used for left phrenic nerve stimulation. Each of the multipolar leads 420 and 430 provide additional electrodes 424, 426 and 434, 436, respectively, for use in delivering an impedance measurement drive current and measuring an impedance signal (which may be a voltage signal). The IMD housing 412 may be used as a common electrode for thoracic impedance measurements. In one embodiment, housing 412 is used with electrode 426 for delivering a drive current and with electrode 424 for measuring a right thoracic impedance measurement. Housing 412 is further paired with electrode 436 for delivering a drive current signal and with electrode 436 for measuring a left thoracic impedance signal.

Left and right thoracic impedance signals may be time or frequency multiplexed to obtain a first impedance signal that has higher sensitivity to changes in right lung volume along a measurement vector 440, shown schematically to extend substantially through right lung 414, and a second impedance signal that has higher sensitivity to changes in left lung volume along a measurement vector 442, shown schematically to extend substantially through left lung 416.

In alternative embodiments, additional subcutaneous or transvenous electrodes may be positioned for facilitating right and left thoracic impedance methods. Such methods may include cardiac electrodes positioned in or on the heart.

Figure 9:
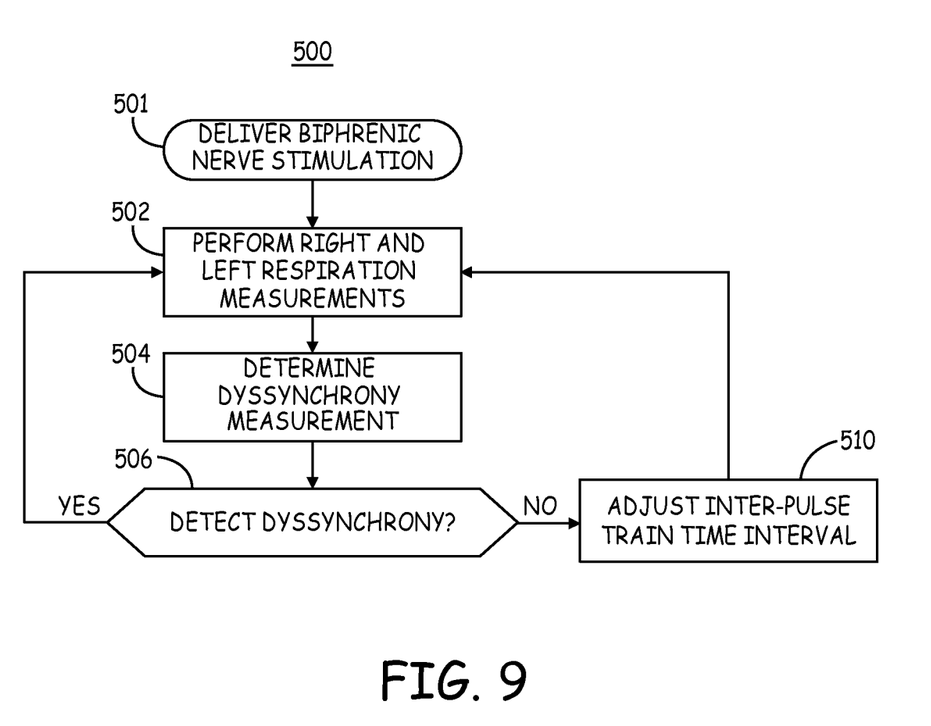
FIG. 9 is a flow chart of a method for using right and left measurements of a respiration response to control biphrenic nerve stimulation.

FIG. 9 is a flow chart 500 of a method for using right and left measurements of a respiration response to control bilateral phrenic nerve stimulation. At block 501, a bilateral phrenic nerve stimulation therapy is delivered according to a programmed therapy protocol. During the therapy, right and left respiration measurements are performed at block 502, such as the right and left thoracic impedance measurements described in conjunction with FIG. 8. Other right and left respiration response measurements may include, but are not limited to, a right and left diaphragm EMG signal or right and left accelerometer signals.

A dyssynchrony measurement is determined at block 504 from the right and left measurements. For example a peak amplitude of each of the right and left measurements may be determined and dyssynchrony may be measured as the time interval between the right and left measurement peaks. Other features or fiducial points of the right and left measurement signals may be identified to provide a time interval measurement correlated to dyssynchrony of the right and left sides of the diaphragm.

The dyssynchrony measurement may be compared to a threshold for detecting diaphragm dyssynchrony at block 506. If the measured time interval is greater than some predetermined threshold, the inter-pulse train interval is adjusted at block 510. If dyssynchrony is not detected, the therapy delivery continues using the existing stimulation parameters. The method returns to block 502 to continue monitoring for dyssynchrony using right and left measurements of the respiration response. Monitoring for dyssynchrony may be performed with every respiration cycle, periodically, or in response to measuring a decrease in a metric of respiration based on an impedance signal or any other measurement of respiration or diaphragm activity.

In the illustrative embodiments, the inter-pulse train time interval is adjusted in response to measuring or detecting dyssynchrony of the right and left sides of the diaphragm. It is contemplated that other nerve stimulation control parameters may influence the synchrony of diaphragmatic stimulation. For example, the pulse amplitude and/or width, frequency of the pulses in the pulse train, number of pulses etc. Since the physiology and anatomy of the right and left phrenic nerves, right and left diaphragm, right and left lungs and airways, and other factors will vary between individual patients and with varying disease state or injury, different responses of the left and right sides of the diaphragm and other respiratory structures may contribute to dyssynchrony of the diaphragm or the overall respiratory response. The location of electrodes and the IMD system will also influence the optimal parameters needed to maximize the synchrony of the respiratory response to biphrenic nerve stimulation. As such, in response to detecting dyssynchrony of the diaphragm activation itself or any measurement correlated to respiratory activity or respiration, adjustment of stimulation control parameters to increase synchrony is not limited to adjustment of the inter-pulse train time interval. Adjustment of any stimulation control parameters that control the pulse energy, pulse frequency, pulse number, or otherwise define the pulse trains delivered to the right and left phrenic nerves and any timing intervals that affect the relative timing of the right and left pulse trains may be adjusted to optimize synchronization of the respiratory response.

Thus, a method and apparatus for providing bilateral phrenic nerve stimulation therapy have been presented in the foregoing description with reference to specific embodiments. It is appreciated that various modifications to the referenced embodiments may be made without departing from the scope of the disclosure as set forth in the following claims.

The invention claimed is:

1. A method for delivering a respiration therapy, comprising:
    delivering a first plurality of stimulation pulses to activate a right portion of a patient's diaphragm and a second plurality of stimulation pulses to activate a left portion of a patient's diaphragm;
    determining dyssynchrony in a respiratory response to the first plurality and the second plurality of stimulation pulses; and
    adjusting a stimulation control parameter controlling the delivering of the first plurality of stimulation pulses and the second plurality of stimulation pulses in response to the dyssynchrony.

2. The method of claim 1 further comprising delivering the first plurality of stimulation pulses transvenously to the right phrenic nerve and delivering the second plurality of stimulation pulses transvenously to the left phrenic nerve.

3. The method of claim 1 wherein adjusting the stimulation control parameter comprises adjusting a time interval between the first plurality of stimulation pulses and the second plurality of stimulation pulses in response to the determined dyssynchrony.

4. The method of claim 1, wherein determining dyssynchrony comprises:
    delivering the first plurality of stimulation pulses to the right phrenic nerve and measuring a first respiration response to the first plurality of stimulation pulses when no stimulation is delivered to the left phrenic nerve;
    delivering the second plurality of stimulation pulses to the left phrenic nerve and measuring a second respiration response to the second plurality of stimulation pulses when no stimulation is delivered to the right phrenic nerve;
    delivering the first plurality of stimulation pulses and the second plurality of stimulation pulses to the respective right and left phrenic nerves and measuring the third respiration response to the bilateral phrenic nerve stimulation; and comparing the first, second and third respiration responses.

5. The method of claim 4 wherein measuring the first, second and third responses comprises measuring a thoracic impedance.

6. The method of claim 4, wherein determining dyssynchrony comprises comparing the third response and a sum of the first response and the second response.

7. The method of claim 1 wherein determining dyssynchrony comprises:
sensing a signal correlated to respiratory activity;
measuring the signal to determine a respiratory response to delivering the first plurality of pulses and the second plurality of pulses during bilateral stimulation; and
determining a feature of the signal indicating a time delay between a response to the first plurality of pulses and a response to the second plurality of pulses.

8. The method of claim 7 wherein measuring the signal comprises measuring a first signal having a greater sensitivity to a respiratory response of a right side of the patient than a left side of the patient and a second signal having a greater sensitivity to a respiratory response of the left side of the patient than the right side of the patient.

9. The method of claim 1 wherein determining dyssynchrony comprises imaging the diaphragm to observe a time delay between activations of the right portion and the left portion of the diaphragm.

10. The method of claim 1 further comprising setting the adjusted stimulation control parameter to a value that causes substantially synchronized contraction of the right portion of the diaphragm and the left portion of the diaphragm.

11. The method of claim 4 further comprising setting the adjusted stimulation control parameter to a value that maximizes the third respiration response.

12. A respiration therapy delivery system, comprising:
a plurality of electrodes for delivering a first plurality of stimulation pulses to activate a right portion of a patient's diaphragm and a second plurality of stimulation pulses to activate a left portion of a patient's diaphragm;
a pulse generator coupled to the plurality of electrodes;
a sensing unit to generate a signal correlated to a respiratory response to the first plurality of stimulation pulses and the second plurality of stimulation pulses;
a control processor configured to determine dyssynchrony in a respiratory response to the first plurality and the second plurality of stimulation pulses and adjust a stimulation control parameter controlling the delivering of the first plurality of stimulation pulses and the second plurality of stimulation pulses in response to the dyssynchrony.

13. The system of claim 12 further comprising a transvenous lead carrying the plurality of electrodes for delivering the first plurality of stimulation pulses transvenously to the right phrenic nerve and for delivering the second plurality of stimulation pulses transvenously to the left phrenic nerve.

14. The system of claim 12 wherein adjusting the stimulation control parameter comprises adjusting a time interval between the first plurality of stimulation pulses and the second plurality of stimulation pulses in response to the determined dyssynchrony.

15. The system of claim 12, wherein determining dyssynchrony comprises:
controlling the pulse generator and the sensing unit to deliver the first plurality of stimulation pulses to the right phrenic nerve and measuring a first respiration response to the first plurality of stimulation pulses when no stimulation is delivered to the left phrenic nerve;
controlling the pulse generator and the sensing unit to deliver the second plurality of stimulation pulses to the left phrenic nerve and measuring a second respiration response to the second plurality of stimulation pulses when no stimulation is delivered to the right phrenic nerve;
controlling the pulse generator and the sensing unit to deliver the first plurality of stimulation pulses and the second plurality of stimulation pulses to the respective right and left phrenic nerves and measuring the third respiration response to the bilateral phrenic nerve stimulation; and
comparing the first, second and third respiration responses.

16. The system of claim 15 wherein the sensing unit is configured to measure thoracic impedance and measuring the first, second and third responses comprises measuring a thoracic impedance.

17. The system of claim 15, wherein determining dyssynchrony comprises comparing the third response and a sum of the first response and the second response.

18. The system of claim 12 wherein determining dyssynchrony comprises:
measuring the signal to determine a respiratory response to delivering the first plurality of pulses and the second plurality of pulses during bilateral stimulation; and
determining a feature of the physiological signal indicating a time delay between a response to the first plurality of pulses and a response to the second plurality of pulses.

19. The system of claim 18 wherein the sensing unit comprises a first sensor for generating a first signal having a greater sensitivity to a respiratory response of a right side of the patient than a left side of the patient and a second sensor for generating a second signal having a greater sensitivity to a respiratory response of the left side of the patient than the right side of the patient.

20. The system of claim 12 wherein the processor is further configured to received data corresponding to an image of the patient for determining dyssynchrony.

21. The system of claim 12 wherein the control processor is configured to adjust an amplitude of one of the first plurality of stimulation pulses and the second plurality of stimulation pulses in response to determining dyssynchrony.

22. The system of claim 12 wherein the control processor is configured to set the adjusted stimulation control parameter to a value that causes substantially synchronized contraction of the right portion of the diaphragm and the left portion of the diaphragm.

23. The system of claim 15 wherein the control processor is further configured to set the adjusted stimulation control parameter to a value that maximizes the third respiration response.

24. A computer-readable medium storing a set of instructions which cause a medical device system to perform a method, the method comprising:
delivering a first plurality of stimulation pulses to activate a right portion of a patient's diaphragm and a second plurality of stimulation pulses to activate a left portion of a patient's diaphragm;
determining dyssynchrony in a respiratory response to the first plurality and the second plurality of stimulation pulses; and adjusting a stimulation control parameter controlling the delivering of the first plurality of stimulation pulses and the second plurality of stimulation pulses in response to the dyssynchrony.

* * * * *